(12) United States Patent
Morawski et al.

(10) Patent No.: US 6,916,292 B2
(45) Date of Patent: Jul. 12, 2005

(54) BONE MARROW ASPIRATOR

(75) Inventors: Linda Morawski, Norton, MA (US);
John C. Voellmicke, Cumberland, RI (US)

(73) Assignee: DePuy Spine, Inc., Raynham, MA (US)

( * ) Notice: Subject to any disclaimer, the term of this patent is extended or adjusted under 35 U.S.C. 154(b) by 287 days.

(21) Appl. No.: 10/194,752

(22) Filed: Jul. 12, 2002

(65) Prior Publication Data

US 2004/0010236 A1 Jan. 15, 2004

(51) Int. Cl.$^7$ .............................................. A61B 10/00
(52) U.S. Cl. ...................................... 600/567; 604/274
(58) Field of Search ................................ 604/22, 93.01, 604/117, 181, 187, 188, 239–241, 264, 272, 274; 600/564–566, 567, 571; 606/92

(56) References Cited

U.S. PATENT DOCUMENTS

| | | | | |
|---|---|---|---|---|
| 2,097,039 A | | 10/1937 | Peterson ...................... 128/347 |
| 3,822,701 A | * | 7/1974 | Cloyd .......................... 604/192 |
| 4,334,538 A | | 6/1982 | Juhn ............................ 128/276 |
| 4,435,170 A | | 3/1984 | Laszczower ................... 604/4 |
| 4,664,128 A | | 5/1987 | Lee .............................. 128/753 |
| 4,681,103 A | * | 7/1987 | Boner et al. ................... 606/1 |
| 4,692,141 A | | 9/1987 | Mahurkar ..................... 604/43 |
| 4,969,870 A | * | 11/1990 | Kramer et al. ............... 604/506 |
| 4,992,226 A | | 2/1991 | Piez et al. .................... 264/109 |
| 5,012,818 A | | 5/1991 | Joishy ......................... 128/754 |
| 5,064,411 A | * | 11/1991 | Gordon, III ................... 604/48 |
| 5,122,114 A | | 6/1992 | Miller et al. .................. 604/49 |
| 5,181,918 A | | 1/1993 | Brandhorst et al. ........... 606/92 |
| 5,357,974 A | | 10/1994 | Baldridge ..................... 128/754 |
| 5,449,351 A | | 9/1995 | Zohmann ..................... 604/272 |
| 5,478,328 A | * | 12/1995 | Silverman et al. ............ 604/272 |
| 5,758,655 A | | 6/1998 | Como Rodriguez et al. ............................ 128/749 |
| 5,848,996 A | | 12/1998 | Eldor ........................... 604/272 |
| 5,902,279 A | | 5/1999 | Powles et al. ................ 604/239 |
| 5,913,859 A | | 6/1999 | Shapira ........................ 606/80 |
| 5,990,382 A | * | 11/1999 | Fox ........................... 623/16.11 |
| 5,993,411 A | * | 11/1999 | Choi ............................ 604/67 |
| 6,022,324 A | | 2/2000 | Skinner ........................ 600/566 |
| 6,033,561 A | | 3/2000 | Schoendorfer ............. 210/195.1 |
| 6,080,115 A | | 6/2000 | Rubinstein ................... 600/567 |
| 6,110,128 A | | 8/2000 | Andelin et al. ............... 600/566 |
| 6,280,424 B1 | | 8/2001 | Chang et al. ................. 604/272 |

FOREIGN PATENT DOCUMENTS

| | | | |
|---|---|---|---|
| EP | 0727187 | 8/1996 | ............ A61B/17/34 |
| GB | 2130890 | 6/1984 | ............ A61B/10/00 |
| GB | 2232599 | 12/1990 | ............ A61M/5/00 |
| WO | 9846295 | 10/1998 | ............ A61M/5/32 |

\* cited by examiner

*Primary Examiner*—Nicholas D. Lucchesi
*Assistant Examiner*—Catherine S. Williams
(74) *Attorney, Agent, or Firm*—Nutter, McClennen & Fish LLP (57) ABSTRACT

A bone marrow aspiration device is provided having a handle adapted to facilitate grasping thereof, and an elongate penetrating element coupled to the handle and having a proximal inlet port and a distal piercing tip for penetrating into tissue and bone. The device is particularly effective in that the configuration of the handle and the elongate penetrating element allows a person to grasp and manipulate the handle while accessing the inlet port to aspirate fluid therethrough. The device is also effective to facilitate penetrating of the device into bone due to the configuration of the distal penetrating tip. A person having ordinary skill in the art will appreciate that, while the device is described for use as a bone marrow aspiration device, the device can be used to withdraw or inject fluid.

35 Claims, 7 Drawing Sheets

BONE MARROW ASPIRATOR

FIELD OF THE INVENTION

The present invention relates to apparatus for infusing liquids, and in particular to a bone marrow aspirator.

BACKGROUND OF THE INVENTION

Bone marrow procedures are commonly performed to diagnose various conditions that affect the different types of blood cells, to diagnose certain cancers to determine the extent of the cancer, and to obtain marrow for transplantation and/or graft preparation. The most frequent site for obtaining bone marrow is through the pelvic bone, known as the ilium. A portion of this bone is readily accessible in most people from the lower back and is usually marked by shallow dimples on either side of the spine. Other aspiration sites include the front of the pelvic bone near the groin and the sternum (chest).

A bone marrow aspiration procedure typically involves passing a bone marrow aspiration needle through the skin and soft tissue and into the bony cortex where the needle enters the spongy bone containing the bone marrow. The needle must be passed into the spongy bone at a sufficient depth before aspiration can be attempted. Once the needle is positioned in the spongy bone, a syringe or other fluid-withdrawing device is attached to the proximal end of the aspirator device and is used to collect the bone marrow. The needle can be repositioned several times to ensure that an adequate amount and/or sufficient sample is retrieved. The bone marrow is then prepared for examination, testing, or further use.

Various needle assemblies are available for aspirating bone marrow. These assemblies typically include a handle with a cannula extending distally from the handle. The handle is used by the physician to apply force to the cannula as the cannula is punctured through tissue and bone. Such needles also typically include a stylet or trocar with a sharpened distal tip which is inserted through the cannula and is used to initially puncture the bone. The stylet or trocar also serves to occlude the cannula while it is penetrating tissue prior to reaching the bone so that the marrow sample subsequently taken is free from unwanted tissue. Once the distal end of the device is positioned within the spongy bone, the stylet or trocar is removed and the syringe can then be connected to the cannula to withdraw bone marrow therethrough.

U.K. Patent No. 2,130,890 of Downs Surgical PLC discloses, for example, an aspiration needle having a transverse-bar, finger-grip handle, and a hollow needle extending distally therefrom. The hollow needle includes several perforations positioned around the distal end for drawing bone marrow therethrough. A stylet is removably positioned through the needle for penetrating the device into bone.

U.S. Pat. No. 4,969,870 of Kramer et al. discloses another aspiration apparatus which is particularly effective to indicate the depth of penetration. The device includes a base for placement against a patient's skin, and an elongated aspiration tube extending through a bore formed in the base. The aspiration tube includes a threaded lower end adapted to penetrate skin.

While these devices can be effective, they can often be difficult to maneuver due to the complexity of the device, as well as the number of parts. One disadvantage of current designs is the necessity to use one hand to do something other than manipulate the marrow retrieval device. The devices typically require a two-handed approach to insert the needle, and further require the additional step of removing the stylet once the needle is positioned, and connecting the syringe to the device. Other disadvantages of current designs include the need to frequently apply extensive rotary motion to the device. The handle must be designed to enable the physician to grasp and manipulate the device, and to apply a sufficient force to the device to puncture the tissue and bone. The shape of the stylet or trocar tip on current devices, however, can make penetrating through bone difficult. The ease of use of a bone marrow biopsy device will minimize the level of trauma visited upon the patient.

Accordingly, there is a need for an improved, user-friendly bone marrow aspiration device.

SUMMARY OF THE INVENTION

The present invention generally provides a bone marrow aspiration device having a handle and an elongate penetrating element coupled to the handle. In one embodiment, the handle includes proximal and distal surfaces, and first and second side surfaces extending between the proximal and distal surfaces. The shape of the handle is preferably adapted to facilitate single-handed use and manipulation thereof. For example, the distal surface of the handle can include one or more finger-receiving recesses. The elongate penetrating element includes a proximal portion coupled to the handle and having a proximal end with an inlet port formed therein, and a distal portion having a smooth outer surface and a solid, distal piercing tip. A substantially cylindrical sidewall defines an inner lumen in the elongate penetrating element which extends from the inlet port to a position proximal to the distal piercing tip. The elongate penetrating element also includes at least one opening formed in the sidewall and in communication with the inner lumen. The opening is preferably positioned proximal to the distal piercing tip. In one embodiment, the proximal portion of the elongate penetrating element is offset with respect to a longitudinal axis of the distal portion of the elongate penetrating element such that the handle of the device can be grasped and manipulated to position the distal portion of the elongate penetrating element while simultaneously allowing access to the inlet port in the proximal portion of the elongate penetrating element.

In a further embodiment, the handle can extend in a direction substantially transverse to the distal portion of the elongate penetrating element. The proximal portion of the elongate penetrating element preferably defines a first axis offset from, but substantially parallel to a second axis defined by the distal portion of the elongate penetrating element. The elongate penetrating element can also include a transverse portion disposed between the proximal and distal portions and oriented substantially transverse to the longitudinal axis of the elongate penetrating element. The transverse portion is preferably disposed within the handle.

In another embodiment, the inlet port in the elongate penetrating element is positioned in the proximal surface of the handle. The handle can include a substantially cylindrical recessed portion which seats the inlet port of the elongate penetrating element. In an exemplary embodiment, the recessed portion is threaded to mate with corresponding threads formed on a surgical syringe. The inlet port can be positioned in a side surface of the handle, and is preferably configured to receive a surgical syringe.

In another embodiment according to the present invention, a bone marrow aspiration device is provided having a handle and an elongate penetrating element having proximal and distal portions. The proximal portion of the elongate penetrating element defines a first axis that extends in a direction substantially transverse to a second axis defined by the distal portion of the elongate penetrating element.

In further aspects of the present invention, the distal piercing tip of the elongate penetrating element can include at least one flat, triangle-shaped surface, an apex of which forms at least a portion of a sharpened distal tip. Preferably, the distal piercing tip includes three triangular surfaces, each having an apex which converges to form a sharpened distal tip. The elongate penetrating element can also include a sidewall having one or more, and preferably three, openings extending therethrough. If three openings are present, each opening is preferably positioned a distance apart from another of the openings along a longitudinal axis of the distal portion of the elongate penetrating element. Further, each opening can be radially offset from another of the openings. In an exemplary embodiment, each opening is positioned about 120° apart from another of the openings around a circumference of the elongate penetrating element.

In yet another embodiment of the present invention, a bone marrow aspirator device is provided having a handle including proximal and distal surfaces extending in a substantially horizontal plane, and an elongate bone penetrating member including a proximal portion having a proximal inlet port and a distal portion having a distal bone penetrating tip. The proximal and distal portions extend in a direction substantially transverse to the horizontal plane of the handle, and the proximal portion of the bone penetrating member has an axis offset from, but substantially parallel to, an axis of the distal portion of the bone penetrating member. The elongate penetrating element further includes an intermediate portion disposed between the proximal and distal portions and oriented to extend substantially parallel to the handle. An inner lumen extends between the proximal portion and the distal portion of the elongate bone, and terminates proximal to the distal bone penetrating tip. At least one opening is formed in the distal portion of the elongate penetrating element proximal to the distal bone penetrating tip. The opening is in communication with the inner lumen.

In further aspects, the intermediate portion is disposed within the handle, and the inlet port is positioned in the proximal surface of the handle. The handle can include a substantially cylindrical recessed portion which seats the inlet port of the elongate bone penetrating member. The recessed portion is preferably threaded to mate with corresponding threads formed on a surgical syringe.

BRIEF DESCRIPTION OF THE DRAWINGS

The invention will be more fully understood from the following detailed description taken in conjunction with the accompanying drawings, in which.

DETAILED DESCRIPTION OF THE INVENTION

In general, the present invention provides a bone marrow aspiration device having a handle adapted to facilitate grasping thereof, and an elongate penetrating element coupled to the handle and having a proximal inlet port and a distal piercing tip for penetrating into tissue and bone. The device is particularly effective in that the configuration of the handle and the elongate penetrating element allow a person to grasp and manipulate the handle while accessing the inlet port to aspirate fluid therethrough. The device is also effective to facilitate penetrating of the device into bone due to the configuration of the distal penetrating tip. A person having ordinary skill in the art will appreciate that, while the device is described for use as a bone marrow aspiration device, the device can be used to withdraw or inject any fluid.

Figure 1:
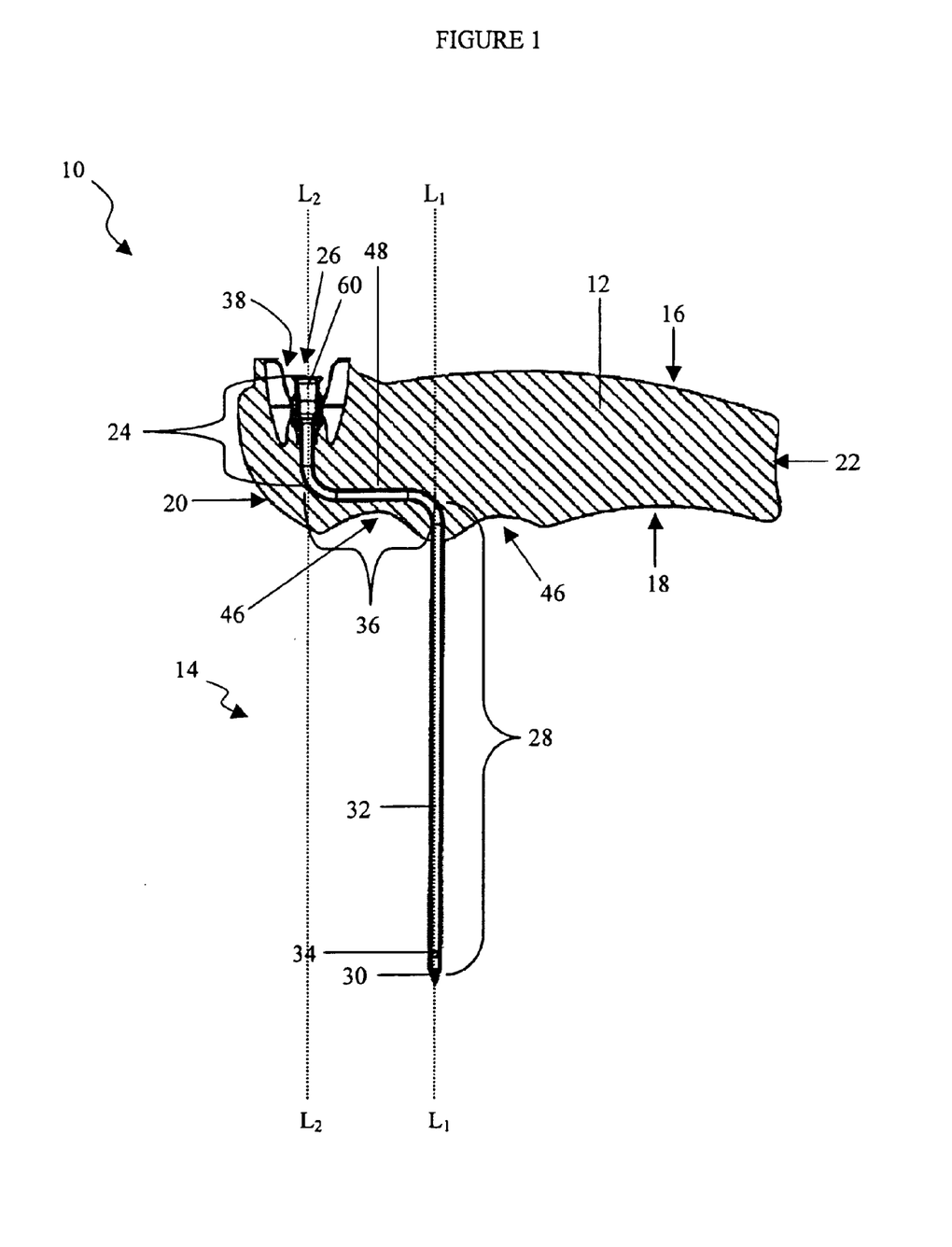
FIG. 1 is a side view illustration of a bone marrow aspiration device having a handle and an elongate penetrating element according to one embodiment of the present invention.

FIG. 1 illustrates one embodiment of a bone marrow aspiration device 10 having a handle 12 and an elongate penetrating element 14 coupled to the handle 12. The elongate penetrating element 14 includes a proximal portion 24 having an inlet port 26 formed therein, a distal portion 28 extending distally from the handle 12 and having a distal piercing tip 30, and an intermediate portion 36 extending between the proximal and distal portions 24, 28. In the illustrated embodiment, proximal portion 24 of the penetrating element 14 is disposed within the handle 12. An inner lumen 32 extends through the elongate penetrating element 14 from the inlet port 26 to a position proximal to the distal end of the elongate penetrating element 14, and preferably to at least one opening 34 formed in the distal portion 28 of the elongate penetrating element 14.

Figure 2A:
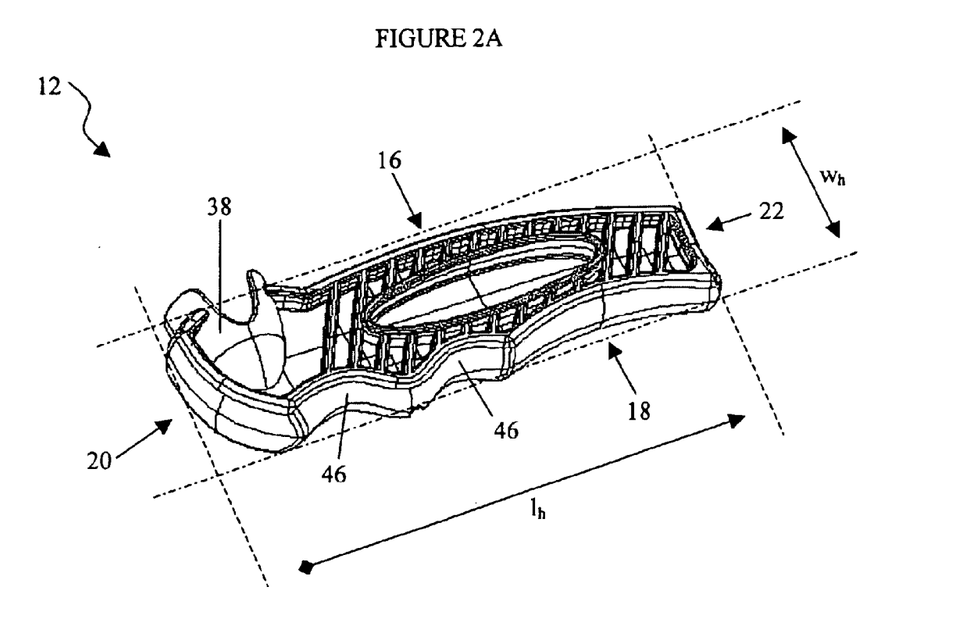
FIG. 2A is a perspective view of the handle of the bone marrow aspiration device shown in FIG. 1.
Figure 2B:
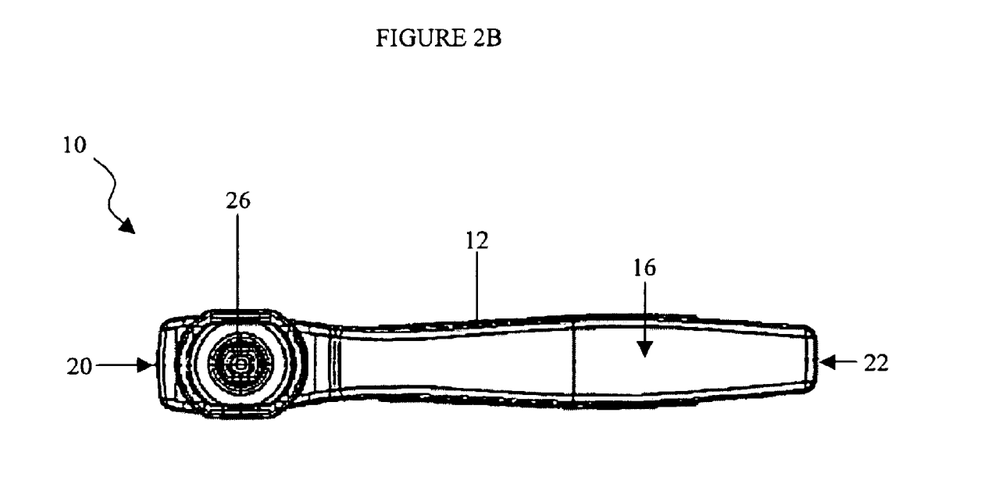
FIG. 2B is a top view of the handle of the bone marrow aspiration device of FIG. 1.

The handle 12 of the bone marrow aspiration device 10 can have virtually any shape and size, but is preferably formed from a solid, rigid body having a shape adapted to facilitate grasping thereof. FIGS. 1–2B illustrate an exemplary embodiment of a handle 12 having an elongate, generally rectangular shape extending in a direction transverse to a longitudinal axis $L_1$ of the elongate penetrating element 14. The handle 12 includes a proximal surface 16, a distal surface 18, and first and second side or end surfaces 20, 22 extending therebetween. While the size of the handle 12 can vary, the handle 12 preferably has a length $l_h$ in the range of about 50 mm to 200 mm, and more preferably about 140 mm, and a width $w_h$ in the range of about 20 mm to 80 mm, and more preferably about 50 mm.

The proximal surface 16 of the handle 12 is preferably adapted to allow access to the inlet port 26 of the elongate penetrating element 14. By way of non-limiting example, the handle 12 can include a receiving well 38 formed in or mated to the proximal surface 16 of the handle 12, as shown in FIGS. 2A–2B. The receiving well 38 can be adapted to seat the base of a medical device, such as a surgical syringe, to enable mating between the medical device and the inlet port 26 on the elongate penetrating element 14. In an exemplary embodiment, as shown, the receiving well 38 has a cylindrical shape which conforms to the shape of the base of a surgical syringe. The receiving well 38 is preferably tapered along the inner surface toward the distal end to provide an interference fit with the base of a surgical syringe, and at least a portion of the receiving well 38 can extend outward from the proximal surface 16 of the handle 12. The receiving well 38 can optionally include a mating element (not shown) for mating with the surgical syringe, or other medical device. While a variety of mating techniques can be used, the receiving well 38 preferably includes threads (not shown) formed on the inner surface thereof. Other suitable mating techniques include, for example, an interference fit and a positive interlock engagement.

The distal surface 18 of the handle 12 can also have a variety of configurations, but preferably includes one or more finger-receiving recesses 46 formed therein to facilitate grasping thereof. A person having ordinary skill in the art will appreciate that the shape, size, and position of the recesses 46 can vary. The handle 12 can also optionally include other grasping members mated to or disposed on the handle 12 for facilitating grasping and manipulation of the handle.

The handle 12 further includes a pathway 48 formed therethrough (shown in FIG. 1) for receiving the elongate penetrating element 14. The pathway 48 can be configured to slidably and/or removably receive the elongate penetrating element 12, or alternatively, it can be molded or sealed around the elongate penetrating element 14 during manufacture of the handle 12. The shape of the pathway 48 will vary depending on the shape of the elongate penetrating element 14. In the embodiment shown in FIG. 1, the pathway 48 extends from the proximal surface 16 to the distal surface 18 of the handle 12. The pathway 48 opening at the proximal surface 16 is positioned along an axis $L_2$ that is offset from, but parallel to the longitudinal axis $L_1$ at which the opening of the pathway 48 along with the distal surface 18 is positioned. A person having ordinary skill in the art will appreciate that a variety of techniques can be used to mate the handle 12 to the elongate penetrating element 14, and that the pathway 48 can have a variety of configurations.

Figure 3A:
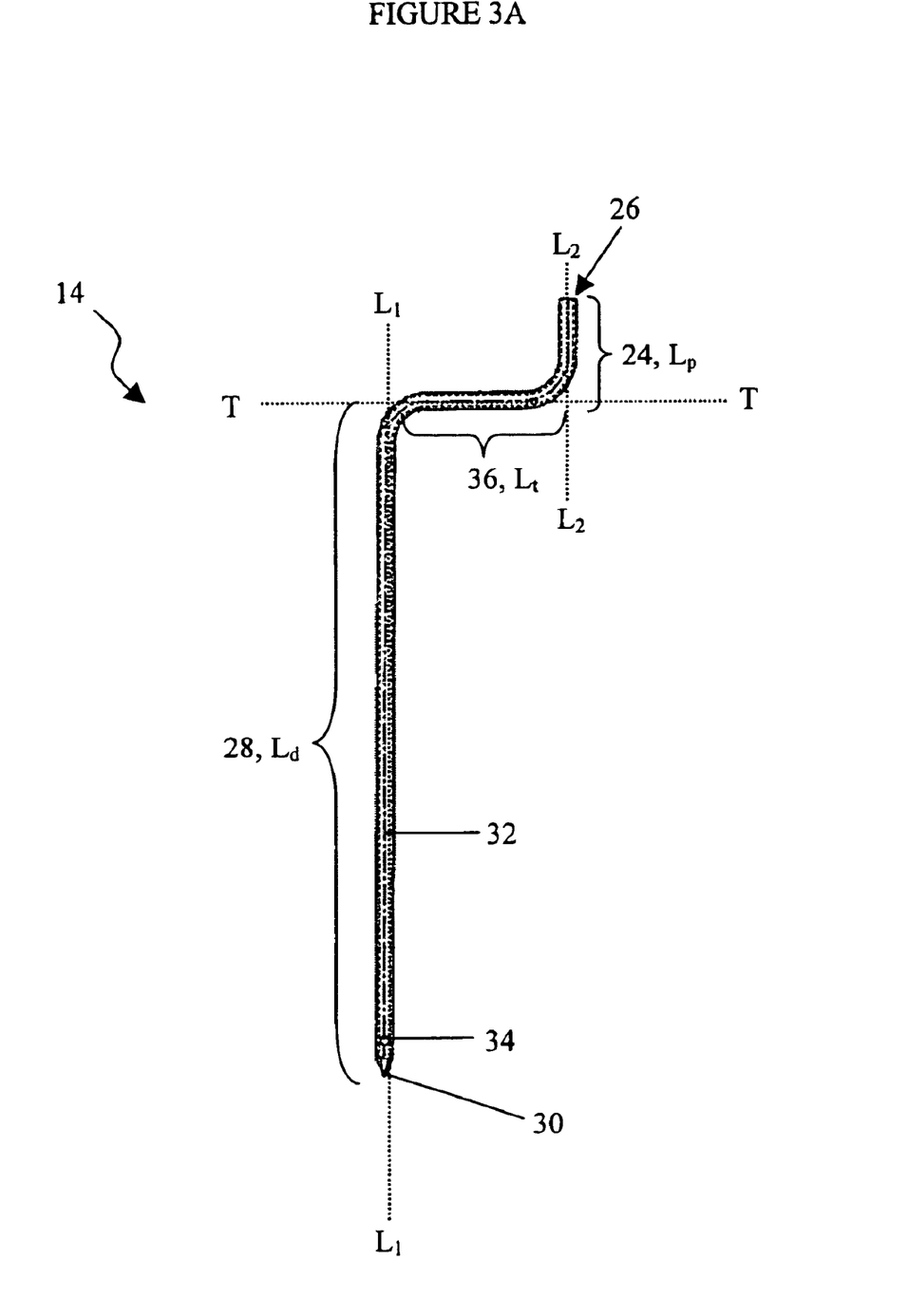
FIG. 3A is a side view illustration of the elongate penetrating element of FIG. 1.

The elongate penetrating element 14 is shown in more detail in FIG. 3A and includes a proximal portion 24 extending along axis $L_2$ and having an inlet port 26, a distal portion 28 having a distal piercing tip 3 and extending along axis $L_1$, which is offset from but parallel to axis $L_2$, and a transverse or intermediate portion 36 extending between the proximal and distal portions 24, 28 along axis T. The transverse portion 36 extends in a direction substantially perpendicular to the proximal and distal portions 24, 28 and preferably lies in the same horizontal plane as the handle 12 (FIG. 1).

The elongate penetrating element 14 can have a variety of shapes and sizes, but preferably has an elongate, cylindrical shape with an inner lumen extending therethrough. The inner lumen 32 preferably extends from the inlet port 26 in the proximal portion 24 of the elongate penetrating element 14 to a position proximal to the distal piercing tip 30. A person having ordinary skill in the art will appreciate that the inner lumen 32 can extend through the distal piercing tip 30 to form an open distal end. This would optionally allow the device 10 to be used with a rigid stylet or trocar known in the art.

Figure 3B:
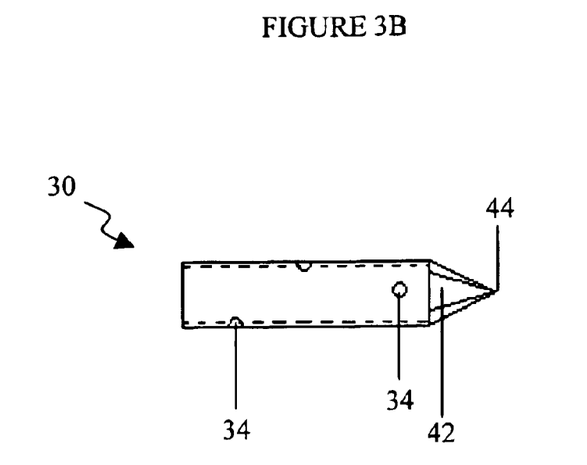
FIG. 3B is a side view of the distal piercing tip of the elongate penetrating element shown in FIG. 3A.

At least one opening 34 is formed in a sidewall of the elongate penetrating element 14 and is in fluid communication with the inner lumen 32. The opening(s) 34, which are preferably positioned proximal to the distal piercing tip 30, can have any shape and size, but the shape and size should be sufficient to enable fluid to flow therethrough. In an exemplary embodiment, several openings are positioned around the elongate penetrating element 14 and are spaced apart both radially and along longitudinal axis $L_1$ of the elongate penetrating element 14. More preferably, the elongate penetrating element 14 includes three openings positioned about 120° apart from one another, as shown in FIG. 3B.

Figure 3C:
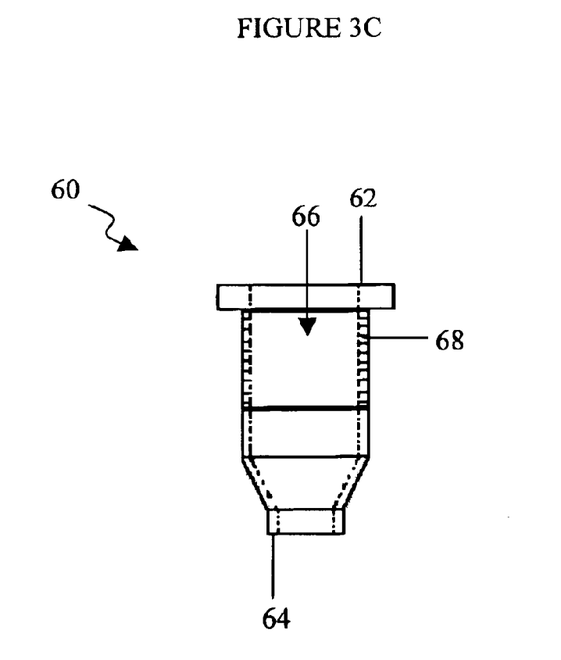
FIG. 3C is a side view of a connector element for use with a bone marrow aspiration device of the present invention.

The proximal portion 24 of the elongate penetrating element 14 includes an inlet port 26 which is preferably adapted to mate with another medical device, such as a surgical syringe. The inlet port 26 can be mated directly to another device, or alternatively can include a connector element 60 mated to the inlet port 26 and in fluid communication with the inner lumen 32 extending through the elongate penetrating element 14. The connector element 60, shown in more detail in FIG. 3C, can have a variety of configurations, and can be fixedly or removably attached to the inlet port 26 at the proximal end of the elongate penetrating element 14. Alternatively, the connector element 60 can be part of the surgical syringe, and the inlet port 26 can be configured to removably mate with the connector element 60. In a preferred embodiment, the connector element 60 is a standard luer lock thread mated to the elongate penetrating element 14 and having a proximal end 62, a distal end 64, and an inner lumen 66 extending there between. The connector element 60 can include threads 68, preferably formed on the inner surface thereof, for mating with corresponding threads formed on a surgical syringe or similar medical device. A person having ordinary skill in the art will appreciate that a variety of different mating mechanisms can be used for coupling a medical device with the inlet port 26 of the elongate penetrating element 14. Suitable techniques for mating a medical device to the inlet port 26 include, for example, a positive interlock engagement, an interference fit, or any other type of engagement element.

The distal portion 28 of the elongate penetrating element 14 includes a distal piercing tip 30 which is adapted to penetrate through tissue and into bone. The tip 30 can have a variety of configurations, but preferably includes at least one triangle-shaped surface 42 having an apex 44 which forms the pointed, distal piercing tip 30. In an exemplary embodiment, the distal piercing tip 30 includes three triangle-shaped surfaces 42, each having the same shape and size and which together merge to form the pointed tip 30. A person having ordinary skill in the art will appreciate that the tip 30 can have virtually any configuration, and can be a closed tip, as shown, or an open tip having a port formed therein. Where an open distal tip is utilized, the device 10 can be used with a trocar or stylet to facilitate penetration into tissue and bone.

While the size of the elongate penetrating element 14 can vary, the length $L_t$ of the transverse portion 26, which is determinative of the distance between the proximal and distal portions 24, 28, is preferably less than the length of the handle $L_h$, and more preferably is in the range of about 20 mm to 40 mm. The length of the proximal and distal portions 24, 28 can also vary, but preferably the proximal portion 24 has a length $L_p$ less than a length $L_d$ of the distal portion 28. In a preferred embodiment, the length $L_p$ of the proximal portion is in the range of about 10 mm to 30 mm, and the length $L_d$ of the distal portion 28 is in the range of about 100 mm to 150 mm.

Figure 4:
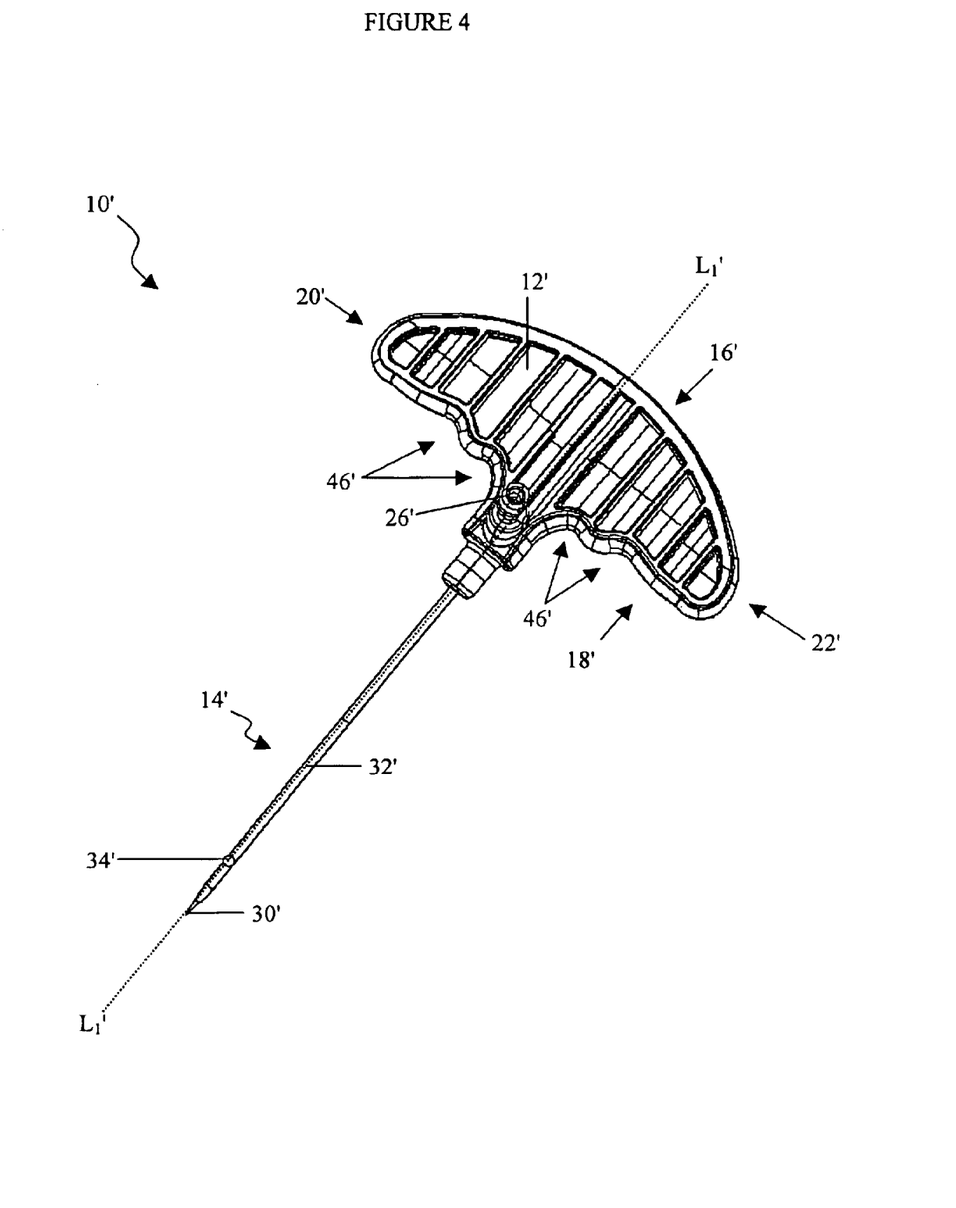
FIG. 4 is a perspective view of a bone marrow aspiration device according to another embodiment of the present invention.
Figure 5:
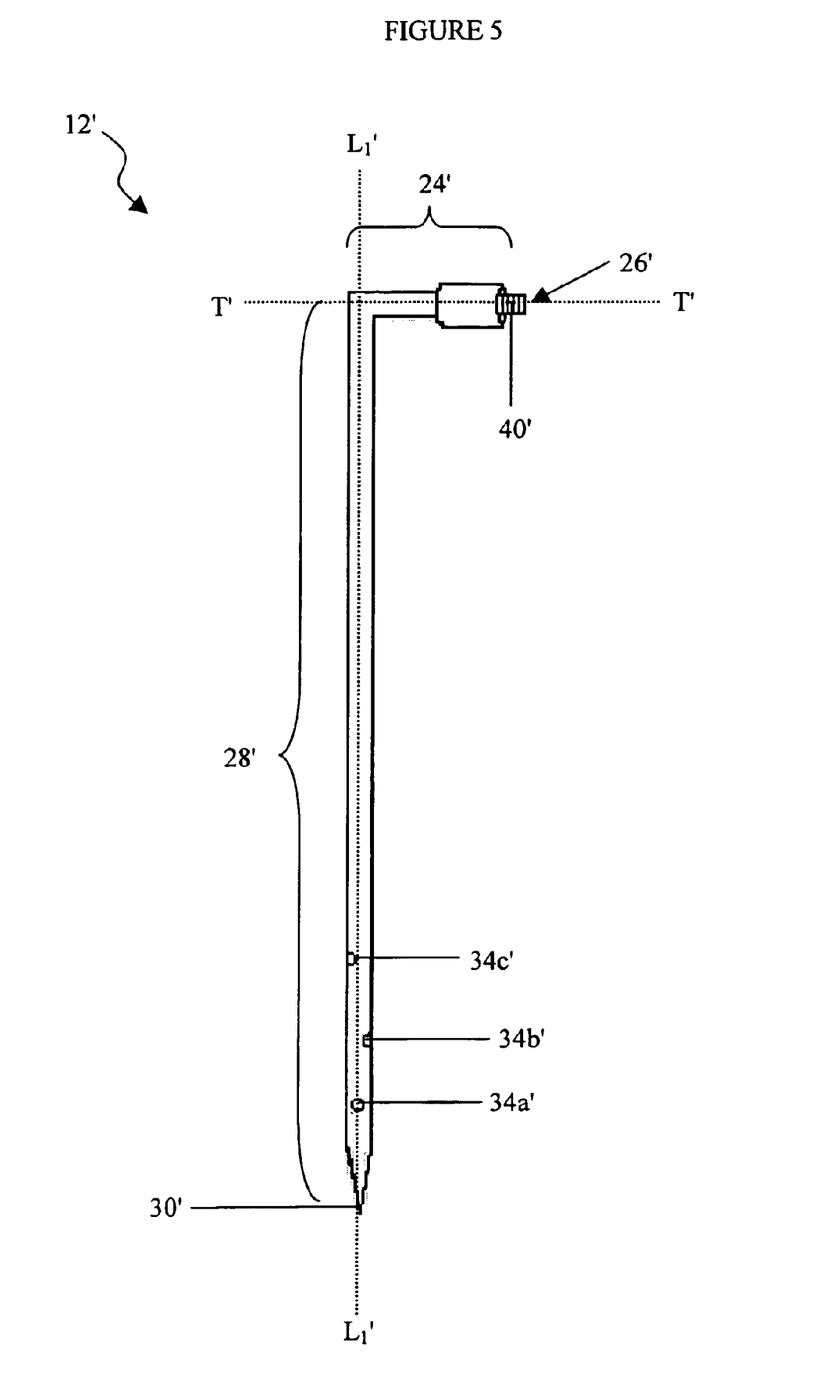
FIG. 5 is a side view illustration of the elongate penetrating element of the bone marrow aspiration device shown in FIG. 4.
Figure 6:
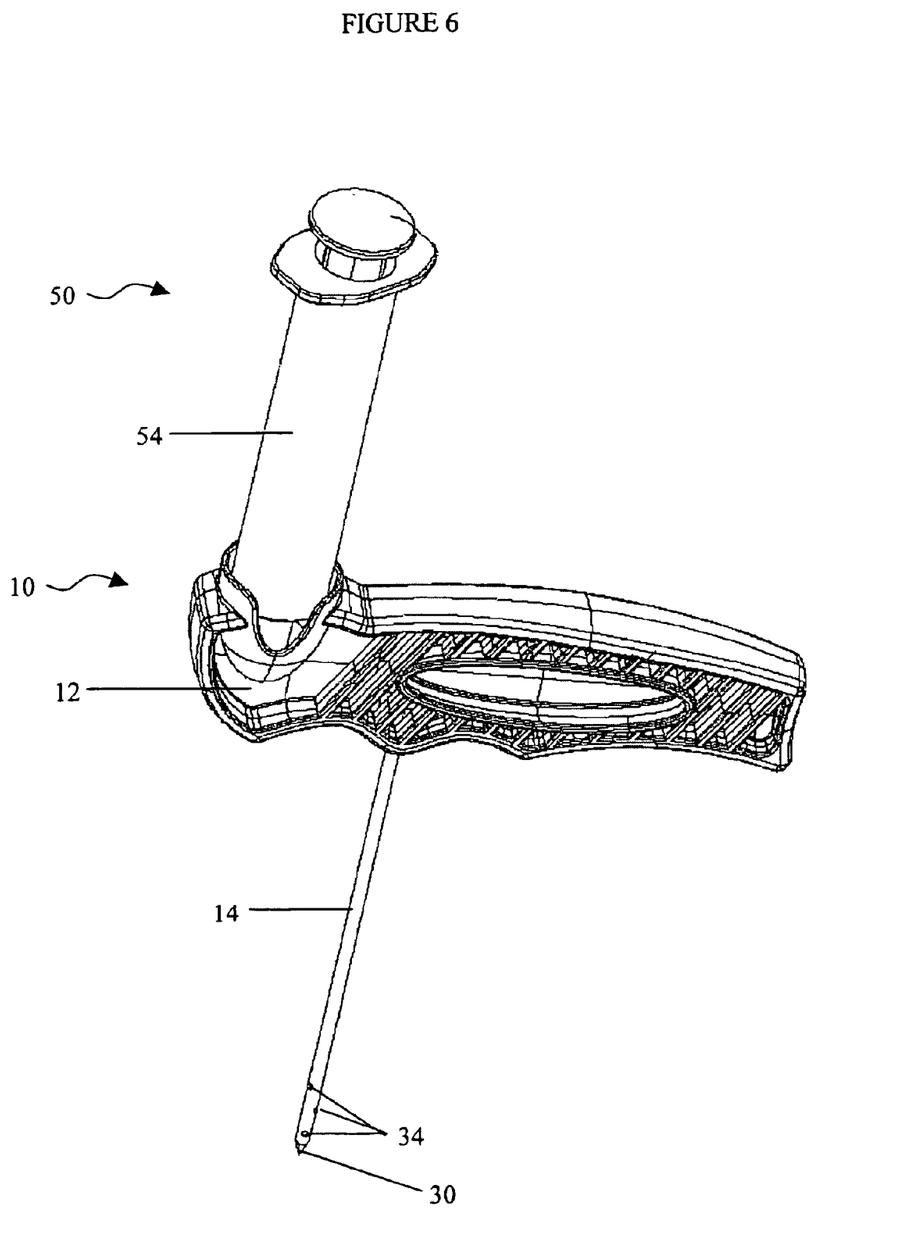
FIG. 6 is a perspective view of the bone marrow aspiration device of FIG. 1 mated to a surgical syringe.

FIG. 4 illustrates another embodiment of a bone marrow aspiration device 10' having a handle 12' and an elongate penetrating element 14'. The handle 12' can have virtually any shape and size, but preferably has an elongate shape extending in a direction substantially transverse to the longitudinal axis of the device 1₁. As shown in FIG. 4, the handle 12' includes a proximal surface 16', a distal surface 18', and first and second side surfaces 20', 22' extending therebetween. The handle 12' should be adapted to facilitate grasping thereof, and can include one or more finger-receiving recesses 46' formed in the distal surface 18' of the handle 12'. A person having ordinary skill in the art will appreciate that the size, shape, and configuration of the handle 12' can vary.

The elongate penetrating element 14' extends through at least a portion of the handle 12', and includes a proximal portion 24' having an inlet port 26', and a distal portion 28' having a distal piercing tip 30'. The inlet port 26, and the distal piercing tip 30' are similar to inlet port 26 and distal piercing tip 30 shown in FIGS. 1 and 3. The inlet port 26' can be positioned in a receiving well similar to receiving well 38 shown in FIG. 1 formed in the handle 12', or it can extend outward from the handle 12'. As shown in FIG. 4, the inlet port 26' and the proximal portion 24' of the device 10' extend outward from a side surface 20' of the handle 12' in a direction substantially transverse to the longitudinal axis $L_1'$ of the distal portion 28' of the elongate penetrating element 14'. As a result, a user can grasp and manipulate the handle 12' while accessing the inlet port 26' to couple a surgical syringe 50 or other medical device to the inlet port 26'.

A person having ordinary skill in the art will appreciate that the elongate penetrating element and the handle can have a variety of configurations, and that the inlet port on the elongate penetrating element can be positioned anywhere around or within the handle.

The handle and elongate penetrating element of the bone marrow aspiration device of the present invention can be constructed from virtually any material that is biologically compatible and suitable for medical applications. One preferred material from which the elongate penetrating element 14, 14' and/or the handle 12, 12' can be made is stainless steel. Other materials from which the elongate penetrating element 14, 14' and/or the handle 12, 12' can be constructed include titanium. The handle 12, 12' can also be made from plastic or other similar materials.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A bone marrow aspiration device, comprising:
   an elongate handle having proximal and distal surface extending between opposed first and second ends, the first and second ends defining a central axis extending therebetween, the handle having a shape adapted to facilitate grasping thereof;
   an elongate penetrating element having
      a proximal portion coupled to the handle and having a proximal end with an inlet port formed therein and positioned at a location on the handle between the opposed first and second ends of the handle,
      a distal portion having a smooth outer surface and a solid, distal piercing tip,
      a substantially cylindrical sidewall defining an inner lumen extending from the inlet port to a position proximal to the distal piercing tip, and
      at least one opening formed in the sidewall and in communication with the inner lumen, the at least one opening being positioned proximal to the distal piercing tip;
   wherein the proximal portion of the elongate penetrating element is offset with respect to a longitudinal axis of the distal portion of the elongate penetrating element such that the handle of the device can be grasped and manipulated to position the distal portion of the elongate penetrating element while simultaneously allowing access to the inlet port in the proximal portion of the elongate penetrating element.

2. The device of claim 1, wherein the central axis of the handle extends in a direction substantially transverse to the longitudinal axis of the distal portion of the elongate penetrating element.

3. The device of claim 1, wherein the proximal portion of the elongate penetrating element defines a longitudinal axis that is offset from, but substantially parallel to the longitudinal axis of the distal portion of the elongate penetrating element.

4. The device of claim 3, wherein the elongate penetrating element includes a transverse portion disposed between the proximal and distal portions and oriented substantially transverse to the longitudinal axis of the proximal and distal portions.

5. The device of claim 4, wherein the transverse portion is disposed within the handle.

6. The device of claim 4, wherein the inlet port comprises a standard threaded luer connector.

7. The device of claim 3, wherein the inlet port is positioned in the proximal surface of the handle.

8. The device of claim 7, wherein the handle includes a substantially cylindrical recessed portion which seats the inlet port of the elongate penetrating element.

9. The device of claim 8, wherein the recessed portion is threaded to mate with corresponding threads formed on a surgical syringe.

10. The device of claim 1, wherein the inlet port is positioned in a side surface of the handle extending between the opposed first and second ends, and connecting the proximal and distal surfaces.

11. The device of claim 10, wherein the proximal portion of the elongate penetrating element defines an axis that extends in a direction substantially transverse to the longitudinal axis defined by the distal portion of the elongate penetrating element.

12. The device of claim 1, wherein the distal piercing tip includes at least one flat, triangle-shaped surface, an apex of which forms at least a portion of a sharpened distal tip.

13. The device of claim 1, wherein the distal piercing tip includes three triangular surfaces, each having an apex which converges to form a sharpened distal tip.

14. The device of claim 1, wherein the sidewall of the elongate penetrating element includes three openings extending therethrough, each opening being positioned a distance apart from another of the openings along the longitudinal axis of the distal portion of the elongate penetrating element.

15. The device of claim 14, wherein each opening in the sidewall of the elongate penetrating element is radially offset from another of the openings.

16. The device of claim 15, wherein each opening is positioned about 120° apart from another of the openings around a circumference of the elongate penetrating element.

17. The device of claim 1, wherein the inlet port of the elongate penetrating element is configured to receive a surgical syringe.

18. The device of claim 1, wherein the distal surface of the handle includes at least one finger-receiving recess.

19. A bone marrow aspirator device, comprising:
- a handle having proximal and distal surfaces extending in a substantially horizontal plane between opposed ends of the handle; and
- an elongate bone penetrating member positioned a distance apart from at least one of the opposed ends of the handle and including
  - a proximal portion having a proximal inlet port and a distal portion having a distal bone penetrating tip, the proximal and distal portions extending in a direction substantially transverse to the horizontal plane of the handle, and the proximal portion of the bone penetrating member having an axis offset from, but substantially parallel to an axis of the distal portion of the bone penetrating member,
  - an intermediate portion disposed between the proximal and distal portions and oriented to extend substantially parallel to the handle,
  - an inner lumen extending between the proximal port and the distal portion of the elongate bone penetrating member, the inner lumen terminating proximal to the distal bone penetrating tip, and
  - at least one opening formed in the distal portion of the elongate penetrating element proximal to the distal bone penetrating tip, the at least one opening being in communication with the inner lumen.

20. The device of claim 19, wherein the intermediate portion is disposed within the handle.

21. The device of claim 19, wherein the inlet port is positioned in the proximal surface of the handle.

22. The device of claim 21, wherein the handle includes a substantially cylindrical recessed portion which seats the inlet port of the elongate bone penetrating member.

23. The device of claim 22, wherein the recessed portion is threaded to mate with corresponding threads formed on a surgical syringe.

24. The device of claim 19, wherein the distal bone penetrating tip includes at least one flat, beveled surface.

25. The device of claim 19, wherein the distal bone penetrating tip includes three triangular surfaces disposed there around, each having an apex which converges to form a sharpened distal tip.

26. The device of claim 19, wherein the at least one opening in the distal portion of the elongate bone penetrating member comprises three openings, each opening being positioned a distance apart from another of the openings along the axis of the distal portion of the elongate bone penetrating member.

27. The device of claim 26, wherein each opening in the sidewall of the elongate bone penetrating member is radially offset from another of the openings.

28. The device of claim 27, wherein each opening is positioned about 120° apart from another of the openings around a circumference of the elongate bone penetrating member.

29. The device of claim 19, wherein the inlet port of the elongate bone penetrating member is configured to receive a surgical syringe.

30. The device of claim 19, wherein the distal surface of the handle includes at least one finger-receiving recess.

31. A bone marrow aspiration device, comprising:
- an elongate handle having at least one side surface extending between opposed ends that define a central axis extending therebetween; and
- a bone penetrating member coupled to the handle at a location offset from a substantial midpoint of the handle, the midpoint being located between the opposed ends, the bone penetrating member including
  - a proximal portion positioned with the handle and having an inlet port located on a side surface of the handle,
  - a distal portion extending from a side surface of the handle at a location that is offset along the central axis of the handle from the location of the inlet port, the distal portion including a distal penetrating tip, and
  - an inner lumen extending from the inlet of the proximal portion through the bone penetrating member to an opening located in the distal portion and positioned proximal to the distal penetrating tip.

32. The device of claim 31, wherein the proximal portion of the bone penetrating member includes a first portion extending from the elongate and defining an axis that is offset from but substantially parallel to an axis of the distal portion, and a transverse portion that extends between the first portion and the distal portion and that defines an axis that is substantially transverse to the axis of the first portion and an axis of the distal portion.

33. The device of claim 31, wherein the at least one side surface of the handle is adapted to facilitate grasping of the handle there around.

34. The device of claim 31, wherein the inlet in the proximal portion is positioned within a recess formed in the handle.

35. The device of claim 34, wherein the recess is adapted to seat a distal end of a surgical syringe.

* * * * *